United States Patent [19]

Robbins et al.

[11] Patent Number: 4,592,662
[45] Date of Patent: Jun. 3, 1986

[54] THERMAL TEST FOR INVESTIGATING FRACTURE MECHANICS OF PRESSURE VESSEL STEELS BY APPLYING THERMAL SHOCK AT HIGH ROTATIONAL SPEEDS

[75] Inventors: Eric J. Robbins; Alan M. Clayton, both of Warrington; William P. White, South Wirral; Robert E. Leckenby, Warrington, all of England

[73] Assignee: United Kingdom Atomic Energy Authority, London, England

[21] Appl. No.: 600,787

[22] Filed: Apr. 16, 1984

[30] Foreign Application Priority Data

Apr. 26, 1983 [GB] United Kingdom ................ 8311382

[51] Int. Cl.$^4$ ........................................... G01N 25/72
[52] U.S. Cl. ....................................... 374/57; 165/61; 374/55
[58] Field of Search ................ 374/4, 5, 57, 50; 165/61; 73/430, 707, 64

[56] References Cited

U.S. PATENT DOCUMENTS

| | | | |
|---|---|---|---|
| 2,167,185 | 7/1939 | Preston | 374/5 |
| 2,596,271 | 5/1952 | Mondet | 73/707 |
| 3,365,930 | 1/1968 | Arias | 374/43 |
| 3,601,184 | 8/1971 | Hauville | 165/54 |
| 3,680,356 | 8/1972 | Felton, Jr. | 374/57 |
| 4,096,754 | 6/1978 | Beveridge, Jr. et al. | 374/117 |
| 4,328,639 | 5/1982 | Cotey | 73/430 |

Primary Examiner—Daniel M. Yasich
Attorney, Agent, or Firm—William R. Hinds

[57] ABSTRACT

Equipment for investigating crack propagation in thick steel plates of a material with applicability for pressure vessels comprises a test specimen in the form of a hollow cylinder of the material under investigation, a vertical spindle from which the hollow cylinder is suspended and which can be rotated at a speed of the order of thousands of revolutions per minute, damping means for damping against flexural resonance vibrations of the cylinder and spindle, a container for the cylinder and means for supplying hot air to the container via a port, means for applying through a port in the container, a jet of cold fluid on to a surface of the cylinder to apply thermal shock thereto the spindle being hollow to accommodate leads from instrumentation on the cylinder to a slip ring unit from which leads to control and recording equipment extend, the instrumentation serving to monitor crack propagation under the conditions of high speed revolution which induce a hoop stress in the material approaching its yield strength, and the thermal shock applied thereto.

11 Claims, 2 Drawing Figures

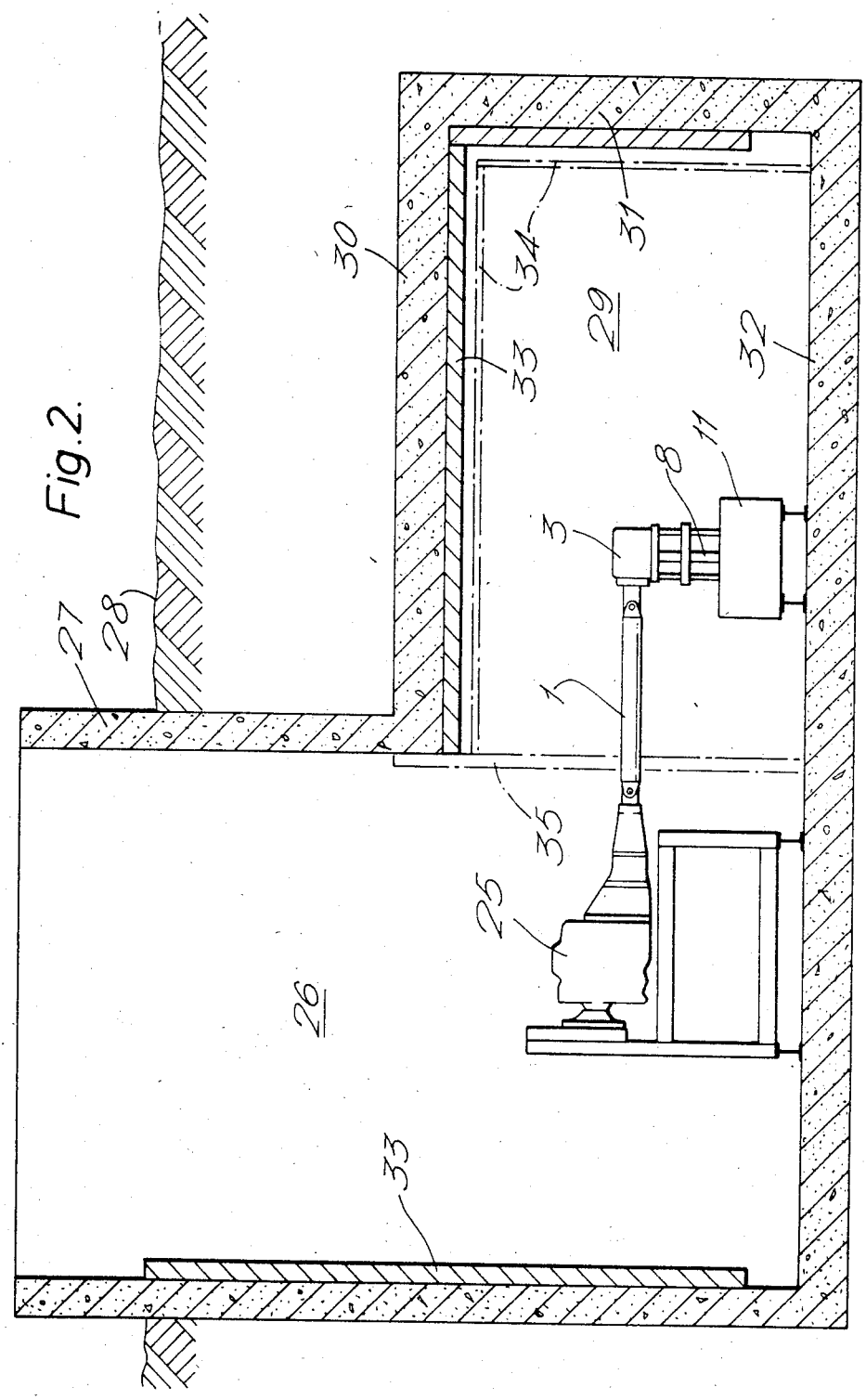

THERMAL TEST FOR INVESTIGATING FRACTURE MECHANICS OF PRESSURE VESSEL STEELS BY APPLYING THERMAL SHOCK AT HIGH ROTATIONAL SPEEDS

This invention relates to equipment for tensile testing, such equipment being particularly suited to investigating the fracture mechanics of pressure vessel steels.

BACKGROUND OF THE INVENTION

Pressure vessels have thick steel walls and so require very large forces to grow cracks. There is a number of different ways of investigating crack propagation in pressure vessel steels, one being to pull on a flat plate of the material using hydraulic equipment. Another involves pneumatically or hydraulically testing a pressure vessel made of the required material but in a scaled-down form compared with the size of pressure vessel for which a typical application of the steel in question, for example, the pressure vessel of a PWR Nuclear Reactor for power generation, can be considered. Each of the foregoing methods has some disadvantages.

Another alternative is axial rotation of a hollow cylinder made of the material in question at a speed sufficient to induce a hoop stress approaching the yield strength of the material, and it is with this method that equipment according to the invention is concerned.

FEATURES AND ASPECTS OF THE INVENTION

According to the invention, equipment for investigating crack propagation in thick steel plates of a material being investigated for pressure vessel application has a test specimen consisting of a hollow cylinder of the material whose wall is of a thickness equivalent to the plate thickness, the hollow cylinder being suspended from a vertical spindle adapted to be rotated at a speed of the order of thousands of revolutions per minute, said cylinder and spindle being damped against flexural resonance vibration, there being means for heating the rotating cylinder and there being also provided means for applying a thermal shock to the rotating cylinder.

The means for heating the rotating cylinder may comprise a container in which the rotating cylinder is disposed, and means for heating the interior of the container to a desired temperature.

The means for applying a thermal shock to the rotating cylinder may comprise means for directing a cold fluid on to a surface of the cylinder whilst it is in rotation.

Advantageously the whole rotating equipment is disposed in an environment with sufficient shielding to avoid danger to operatives should there be a failure of the specimen.

DESCRIPTION OF THE DRAWINGS

Constructional features of an example of equipment for investigating crack propagation is pressure vessel steels and embodying the invention will now be described with reference to the accompanying drawings, wherein:

FIG. 2 is a view to a smaller scale and showing the disposition of the equipment in a safety environment.

DESCRIPTION OF THE PREFERRED EMBODIMENT

Figure 1:
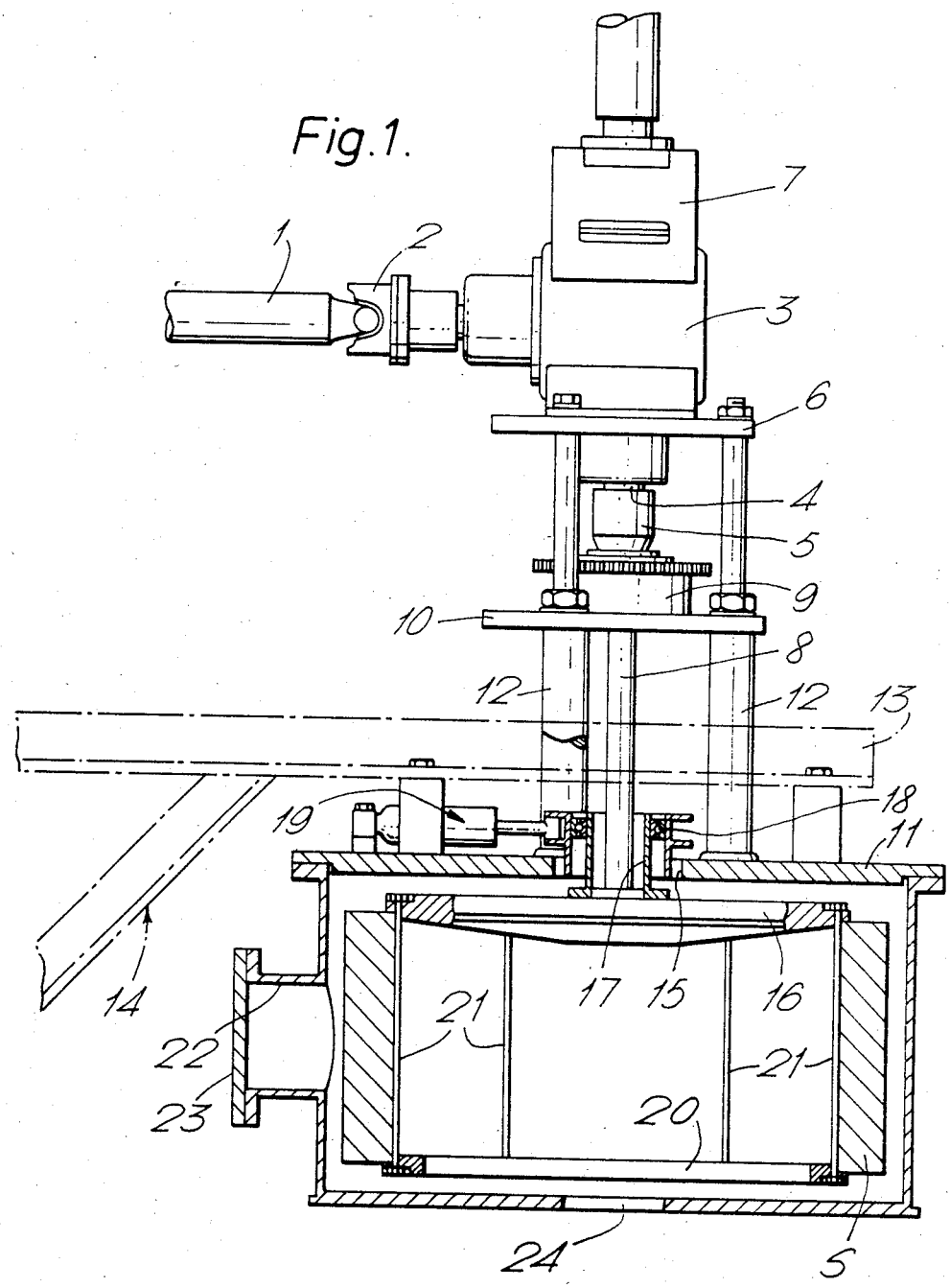
FIG. 1 is a side view partly in medial section.

Referring firstly to FIG. 1 of the drawings, we provide equipment for investigating crack propagation of pressure vessel steels, such equipment incorporating a driven shaft 1 adapted to be rotated by a conventional prime mover (see FIG. 2 which shows a prime mover 25) at an angular speed in the region of thousands of revolutions per minute. The shaft 1 is connected through a universal coupling 2 to a gear box 3 whose output spindle 4 drives a gear coupling 5. The gear box 3 is mounted on a platform 6. The gear coupling 5 drives a hollow specimen drive spindle 8 which is carried in support bearings 9 carried on another platform 10. An apertured box 11 is suspended by ties 12 from the platform 10, the box 11 being also attached to a cantilever arm 13 of a welded framework support structure 14. The spindle 8 entends into the box 11 through an aperture 15 therein and the lower end of spindle 8 has a specimen support disc 16 secured to it for rotation therewith. Also secured to the support disc is an upstanding sleeve 17 which has a ball bearing 18 for rotation therewith, the outer race of the bearing 18 being engaged by one or more hydraulic dampers 19, serving to damp the rotating specimen and spindle against flexural resonance vibrations.

The support disc 16 has a lower annular ring 20 suspended from it by tie rods 21. Surrounding the tie rods 21 is a specimen, referenced S, of the material being investigated, and consisting of a hollow cylinder of pressure vessel steel. Such a cylinder can be of thick plate either bent and welded, or forged, to cylindrical form. Electrical connections to thermocouples and strain gauges (not shown) on the specimen S are taken up the hollow drive spindle 8, through the gear box 3, to a slip ring unit 7, from which they are led to stationary control and recording instruments (not shown). The tie rods 21 are tightened sufficiently to integrate the specimen with the disc 16 for rotation therewith at high speed, The box 11 has a port 22 and a gate valve 23 by means of which hot air can be supplied to the interior of the box 11, and an array of cooling water jets (not shown) extends upwardly through an aperture 24 in the lower end of box 11 and through the annular plate 20 so that cooling water can be made to impinge on the inner surface of the specimen S. The hot air environment in box 11 and the cooling water jets directed on the inner surface of the specimen can be arranged to place the specimen in a desired condition of thermal shock.

Testing for crack propagation is performed by forming an artificial crack of known dimensions in the specimen S, causing the specimen S to be rotated at a speed which induces a hoop stress approaching the yield strength of the material with hot air supplied to the box 11 such that the temperature of the specimen S approximates to that of the pressure vessel of an operating nuclear reactor, introducing the cold water jets so as to cause a desired condition of thermal shock to the specimen, measurable by the thermocouples, and measuring the amount of crack propagation, from nil to catastrophic, by the strain gauges and other instrumentation with which the specimen S is provided.

Referring now to FIG. 2, provision for ensuring the safety of operatives is indicated diagrammatically. The prime mover of the equipment is designated 25 and is conventional and can, for example, be an electric motor and is disposed in a compartment 26 provided in a concrete emplacement 27 below soil level indicated by reference numeral 28. An adjoining compartment 29 is provided with a concrete top 30, a concrete side 31 and a concrete base 32 which is common with the base of the compartment 26. The compartments 26 and 29 can additionally be provided with timber lining 33 and there can additionally be linings 34 of steel plates and provision for dividing the compartments 26 and 29 by a steel plate 35. The shaft 1, reduction gear 3, rotating spindle 8, bearings 9, box 11 and associated equipment are contained in the compartment 29, the compartment 26 being open at the top for access to the prime mover.

Advantages of the rotating cylinder test equipment include, firstly, the fact that very high hoop stresses can be induced in cylinders of any practical wall thickness. The limitation to stress and thickness is governed only by the maximum speed of the drive motor and the maximum weight that can be held by the support bearings. The tensile hoop forces that can be generated exceed those attainable in the largest hydraulic test machines. Secondly the stress distribution across the specimen thickness approximates to that in a pressure vessel, with only the absence of biaxiality, which is not important in influencing fracture or plastic collapse. Thirdly thermal shocks can readily be induced in the specimen, with very high heat transfer coefficients, as in a PWR pressure vessel under emergency cooling, and lastly the cost of the test equipment is modest compared with that of servohydraulic equipment.

We claim:

1. Equipment for investigating crack propagation in thick plates of a steel material of predetermined thickness under investigation for pressure vessel applications, comprising a test specimen in the form of a hollow cylinder of the material, the wall thickness of the cylinder being equivalent to the predetermined thickness of the plates, a vertical spindle for rotation at a speed of the order of thousands of revolutions per minute and from which said hollow cylinder is suspended so as in operation to induce substantial hoop stresses in the cylinder, damping means for damping against flexural resonance vibrations of said cylinder and spindle, means for heating the rotating cylinder to a temperature approximating to the expected operating temperature of the pressure vessel, and means for applying a desired amount of thermal shock to the rotating cylinder.

2. Equipment according to claim 1, wherein the means for heating the rotating cylinder comprises a container in which the rotating cylinder is disposed, and means for heating the interior of the container to a desired temperature.

3. Equipment according to claim 2, wherein the last-named means for heating comprises heated air within the container.

4. Equipment according to claim 3, wherein the means for applying a thermal shock to the rotating cylinder comprise means for directing a cold fluid on to a surface of the cylinder whilst the cylinder is in rotation.

5. Equipment according to claim 4, wherein the cold fluid is directed on to the interior surface of the rotating cylinder.

6. Equipment according to claim 2, wherein the means for applying a thermal shock to the rotating cylinder comprise means for directing a cold fluid on to a surface of the cylinder whilst the cylinder is in rotation.

7. Equipment according to claim 6, wherein the cold fluid is directed on to the interior surface of the rotating cylinder.

8. Equipment according to claim 1, wherein the means for applying a thermal shock to the rotating cylinder comprise means for directing a cold fluid on to a surface of the cylinder whilst the cylinder is in rotation.

9. Equipment according to claim 8, wherein the cold fluid is directed on to the interior surface of the rotating cylinder.

10. Equipment according to claim 1, wherein the said vertical spindle is hollow, and electrical connections from monitoring equipment on the cylinder are led through the hollow spindle to a slip ring unit from which extend leads to stationary control and recording instrumentation.

11. Equipment according to claim 1, disposed in an environment with sufficent shielding to avoid danger to operatives should there be a failure of the rotating cylinder.

* * * * *

UNITED STATES PATENT AND TRADEMARK OFFICE
CERTIFICATE OF CORRECTION

PATENT NO. : 4,592,662
DATED : June 3, 1986
INVENTOR(S) : Eric J. Robbins et al

It is certified that error appears in the above-identified patent and that said Letters Patent is hereby corrected as shown below:

The Title should read as follows:

-- [54] EQUIPMENT FOR INVESTIGATING FRACTURE MECHANICS OF PRESSURE VESSEL STEELS BY APPLYING THERMAL SHOCK AT HIGH ROTATIONAL SPEEDS--.

Signed and Sealed this

Twenty-third Day of September 1986

[SEAL]

Attest:

DONALD J. QUIGG

Attesting Officer     Commissioner of Patents and Trademarks